United States Patent
Lemonis

(10) Patent No.: US 11,147,710 B2
(45) Date of Patent: Oct. 19, 2021

(54) CALCULATION OF ACTUAL ASTIGMATISM CORRECTION AND NOMOGRAPHS FOR CORNEAL LASER TREATMENT

(71) Applicant: Alcon Inc., Fribourg (CH)

(72) Inventor: Sissimos Lemonis, Schwaig (DE)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 15/751,126

(22) PCT Filed: Feb. 10, 2017

(86) PCT No.: PCT/IB2017/050761
§ 371 (c)(1),
(2) Date: Feb. 7, 2018

(87) PCT Pub. No.: WO2018/146519
PCT Pub. Date: Aug. 16, 2018

(65) Prior Publication Data
US 2020/0085621 A1 Mar. 19, 2020

(51) Int. Cl.
*A61F 9/008* (2006.01)
(52) U.S. Cl.
CPC .. *A61F 9/00806* (2013.01); *A61F 2009/0088* (2013.01); *A61F 2009/00859* (2013.01); *A61F 2009/00872* (2013.01); *A61F 2009/00882* (2013.01)
(58) Field of Classification Search
CPC ............................................. A61F 2009/00859
See application file for complete search history.

(56) References Cited

U.S. PATENT DOCUMENTS

| | | | |
|---|---|---|---|
| 7,044,944 B2 * | 5/2006 | Campin | A61B 3/1015 128/898 |
| 2003/0078753 A1 | 4/2003 | Campin et al. | |
| 2006/0007397 A1 | 1/2006 | Lai | |
| 2009/0216218 A1 | 8/2009 | Somani et al. | |
| 2016/0150952 A1 | 6/2016 | Raymond et al. | |

FOREIGN PATENT DOCUMENTS

| | | |
|---|---|---|
| CN | 101715335 A | 5/2010 |
| CN | 102136063 A | 7/2011 |
| EP | 1719483 A1 | 11/2006 |

(Continued)

OTHER PUBLICATIONS

Anastasios John Kanellopoulos; "Topography-modified refraction (TMR): adjustment of treated cylinder amount and axis to the topography versus standard clinical refraction in myopic topography-guided LASIK"; Clinical Ophthalmology; vol. 2016:10; pp. 2213-2221; downloaded from https://www.dovepress.com/.

(Continued)

*Primary Examiner* — Michael W Kahelin

(57) ABSTRACT

A method for to calculation of actual astigmatism correction and nomographs for corneal laser treatment includes performing a post-operative measurement of the cornea of a patient to determine actual astigmatism coefficients. The actual astigmatism coefficients are compared against the expected astigmatism coefficients to generate a nomograph value or a nomograph curve over a sample population. The nomograph is used to calibrate subsequent laser treatments for improved accuracy of clinical results.

18 Claims, 4 Drawing Sheets

(56) References Cited

FOREIGN PATENT DOCUMENTS

| JP | 2006523519 A | 10/2006 |
|----|--------------|---------|
| JP | 2008501459 A | 1/2008 |
| JP | 2011518028 A | 6/2011 |
| WO | 2016153133 A1 | 9/2016 |

OTHER PUBLICATIONS

Nam, et al., "Weighted Zernike expansion with applications to the optical aberration of the human eye", Oct. 2005, pp. 1709-1716, vol. 22, No. 9, Journal of the Optical Society of America A.

Shojanazeri, et al., "Suitability of Zernike Moments for General Image Retrieval", Jul. 2016, pp. 34-42, vol. 21, No. 4, Journal of Xi'an University of Posts and Telecommunications.

* cited by examiner

400 — METHOD FOR CALCULATING NOMOGRAPHS FOR CORNEAL LASER TREATMENT

402 CALCULATING AN EXPECTED ASTIGMATISM COEFFICIENT FOR A PATIENT SUBJECT TO A FIRST CORNEAL LASER TREATMENT AS A FIRST DIFFERENCE BETWEEN A PRE-OPERATIVE ASTIGMATISM COEFFICIENT AND A CORRECTION ASTIGMATISM COEFFICIENT, WHEREIN THE PRE-OPERATIVE ASTIGMATISM COEFFICIENT REPRESENTS A FIRST MEASUREMENT OF A CORNEA OF THE PATIENT BEFORE THE FIRST CORNEAL LASER TREATMENT, AND THE CORRECTION ASTIGMATISM COEFFICIENT REPRESENTS CHANGES TO THE CORNEA PLANNED FOR THE FIRST CORNEAL LASER TREATMENT

404 RECEIVING AN INDICATION THAT THE FIRST CORNEAL LASER TREATMENT ON THE CORNEA OF THE PATIENT WAS PERFORMED ACCORDING TO THE CORRECTION ASTIGMATISM COEFFICIENT

406 RECEIVING AN ACTUAL ASTIGMATISM COEFFICIENT OF THE CORNEA OF THE PATIENT, WHEREIN THE ACTUAL ASTIGMATISM COEFFICIENT REPRESENTS A SECOND MEASUREMENT OF THE CORNEA AFTER A TIME PERIOD AFTER THE FIRST CORNEAL LASER TREATMENT

408 CALCULATING A NOMOGRAPH VALUE BASED ON A SECOND DIFFERENCE BETWEEN THE EXPECTED ASTIGMATISM COEFFICIENT AND THE ACTUAL ASTIGMATISM COEFFICIENT

410 USING THE NOMOGRAPH VALUE TO CALIBRATE THE CORRECTION ASTIGMATISM COEFFICIENT FOR A SUBSEQUENT CORNEAL LASER TREATMENT ON ANOTHER PATIENT, WHEREIN THE SECOND DIFFERENCE FOR THE SUBSEQUENT CORNEAL LASER TREATMENT ON THE OTHER PATIENT IS SMALLER THAN THE SECOND DIFFERENCE FOR THE FIRST CORNEAL LASER TREATMENT

FIG. 4

CALCULATION OF ACTUAL ASTIGMATISM CORRECTION AND NOMOGRAPHS FOR CORNEAL LASER TREATMENT

BACKGROUND

Field of the Disclosure

The present disclosure relates to ophthalmic surgery, and more specifically, to calculation of actual astigmatism correction and nomographs for corneal laser treatment.

Description of the Related Art

The human eye includes a cornea and a crystalline lens that are intended to focus light that enters the pupil of the eye onto the retina. However, the eye may exhibit various refractive errors which result in light not being properly focused upon the retina, and which may reduce visual acuity. Ocular aberrations can range from the relatively simple and by means of glasses or contact lenses correctable spherical and cylindrical errors that cause myopia, hyperopia, or regular astigmatism, and which are correctable by means of eyeglasses or contact lenses. Some ocular aberrations may include more complex refractive errors that are not correctable by classical correction methods, such as spherical and cylindrical corrections, and can cause, for example, halos and starbursts in a person's vision. The more complex refractive errors, such as astigmatism, can also influence the perceived sphere and cylinder correction subjectively accepted by the patient.

Many interventions have been developed over the years to correct various ocular aberrations. These include spectacles, contact lenses, corneal refractive surgery, such as laser-assisted in situ keratomileusis (LASIK) or corneal implants, and intraocular lenses (IOLs). The diagnosis and specification of sphero-cylindrical spectacles and contact lenses for treatment of myopia, hyperopia, and astigmatism are well-established. Some surgery-based techniques, such as LASIK to reshape the cornea, are in wide-spread use and can yield good corrective results, but may not be as predictable as desired. In particular, LASIK for astigmatism correction may result in varying outcomes for different patients, which is undesirable.

SUMMARY

In one aspect, a disclosed method is for calculating nomographs for corneal laser treatments. The method may include calculating an expected astigmatism coefficient for a patient subject to a first corneal laser treatment as a first difference between a pre-operative astigmatism coefficient and a correction astigmatism coefficient. In the method, the pre-operative astigmatism coefficient may represent a first measurement of a cornea of the patient before the first corneal laser treatment, while the correction astigmatism coefficient may represent changes to the cornea planned for the first corneal laser treatment. The method may also include receiving an indication that the first corneal laser treatment on the cornea of the patient was performed according to the correction astigmatism coefficient. The method may further include receiving an actual astigmatism coefficient of the cornea of the patient. In the method, the actual astigmatism coefficient may represent a second measurement of the cornea after a time period after the first corneal laser treatment. The method may still further include calculating a nomograph value based on a second difference between the expected astigmatism coefficient and the actual astigmatism coefficient, and using the nomograph value to calibrate the correction astigmatism coefficient for a subsequent corneal laser treatment on another patient. In the method, the second difference for the subsequent corneal laser treatment on the other patient may be smaller than the second difference for the first corneal laser treatment.

In any of the disclosed embodiments of the method, the nomograph value may be specific to a laser system for performing the corneal laser treatment and the subsequent corneal laser treatment.

In any of the disclosed embodiments of the method, the nomograph value may be specific to a surgeon performing the corneal laser treatment and the subsequent corneal laser treatment.

In any of the disclosed embodiments of the method, the nomograph value may be specific to a type of the corneal laser treatment and the subsequent corneal laser treatment.

In any of the disclosed embodiments of the method, the nomograph value may be calculated based on a sample population of patients. In the method, the pre-operative astigmatism coefficient, the correction astigmatism coefficient, the expected astigmatism coefficient, the actual astigmatism coefficient, and the second difference may be determined for each patient in the sample population.

In any of the disclosed embodiments of the method, the nomograph value may be calculated as an empirical function of the actual astigmatism coefficient versus the expected astigmatism coefficient for the sample population.

In any of the disclosed embodiments of the method, a data point of the empirical function may be determined using a median value of the actual astigmatism coefficient.

In any of the disclosed embodiments of the method, the empirical function may be calculated using curve fitting of a plurality of the data points.

In any of the disclosed embodiments of the method, the pre-operative astigmatism coefficient, the correction astigmatism coefficient, the expected astigmatism coefficient, the actual astigmatism coefficient may be a Zernike coefficient selected from one of: $Z_3$, $Z_5$, $Z_{11}$, and $Z_{13}$.

In any of the disclosed embodiments of the method, the time period may be three months.

Other disclosed aspects include an astigmatism nomograph system including a processor having access to memory media storing instructions executable by the processor to implement the method. In another aspect, the astigmatism nomograph system may be integrated within a laser system for performing corneal laser treatments, such as a LASIK system.

BRIEF DESCRIPTION OF THE DRAWINGS

For a more complete understanding of the present invention and its features and advantages, reference is now made to the following description, taken in conjunction with the accompanying drawings, in which:

FIG. 4 is a flow chart of selected elements of a method for calculating nomographs for corneal laser treatment.

DESCRIPTION OF PARTICULAR EMBODIMENT(S)

Figure 1:
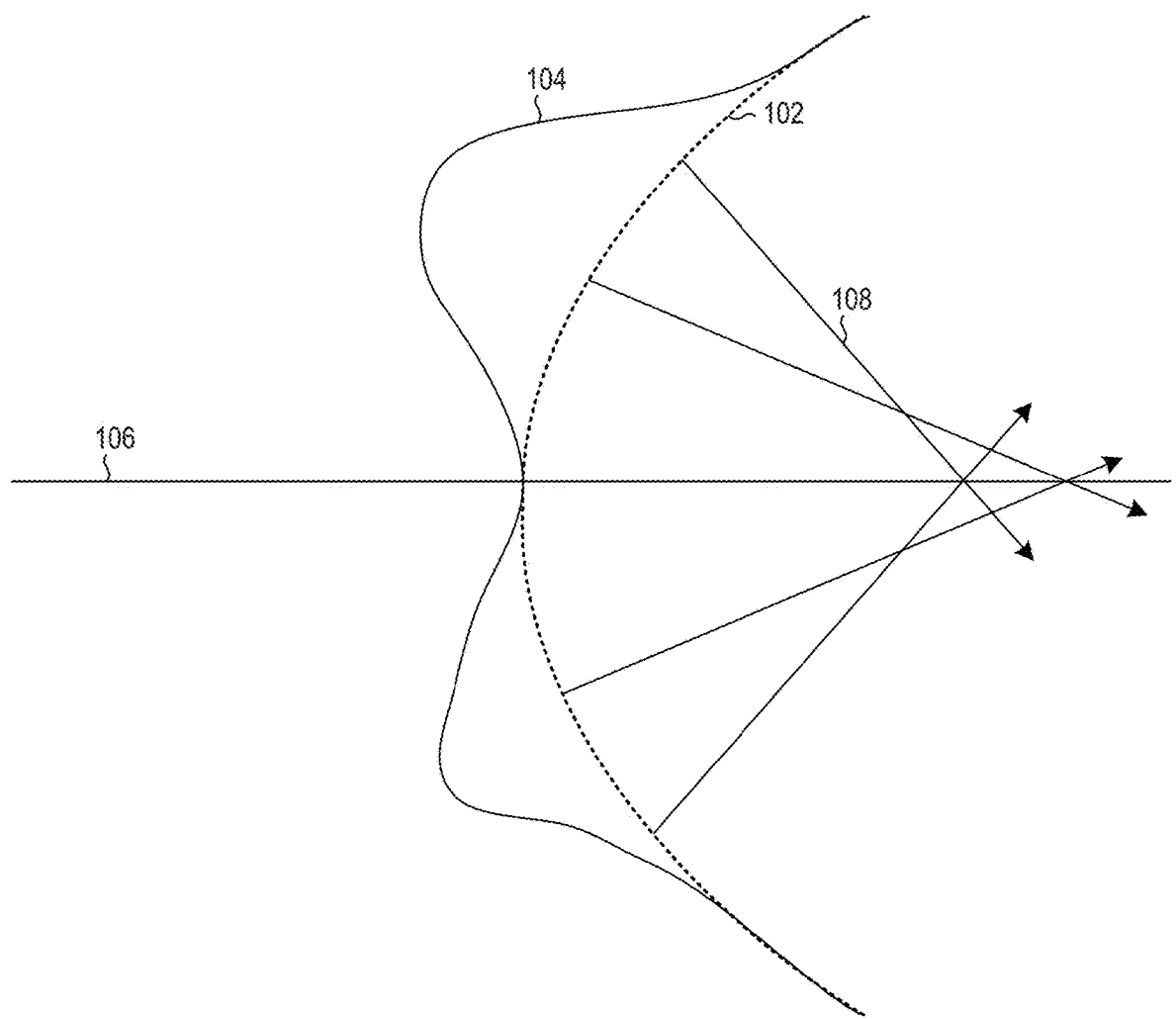
FIG. 1 is a depiction of spherical aberration of the cornea.

In the following description, details are set forth by way of example to facilitate discussion of the disclosed subject matter. It should be apparent to a person of ordinary skill in the field, however, that the disclosed embodiments are exemplary and not exhaustive of all possible embodiments.

Throughout this disclosure, a hyphenated form of a reference numeral refers to a specific instance of an element and the un-hyphenated form of the reference numeral refers to the element generically or collectively. Thus, as an example (not shown in the drawings), device "12-1" refers to an instance of a device class, which may be referred to collectively as devices "12" and any one of which may be referred to generically as a device "12". In the figures and the description, like numerals are intended to represent like elements.

As noted above, various ophthalmological techniques have been developed to correct ocular aberrations to improve the vision of patients. In particular, astigmatism represents a higher order refractive error that can affect the cornea (corneal astigmatism) or the eye lens (lenticular astigmatism) and is different from other refractive errors such as myopia or hyperopia. For example, corneal astigmatism (also referred to herein below as simply 'astigmatism') may result from an irregular shape of the cornea that can result in both near and far objects appearing blurry, among other visual distortions.

More recently, LASIK has been used to treat or mitigate astigmatism by modifying the topographic shape of the cornea. Accordingly, the desired corrections for astigmatism may be obtained by determining a shape of the cornea using a topographical or wavefront analysis, and then applying a curve fitting technique to determine an actual degree of corneal astigmatism. The curve fitting technique may apply specific higher order functions that are associated with astigmatism and determine one or more coefficients that are indicative of the corneal fit to the higher order astigmatism functions. Then, based on these 'pre-operative astigmatism coefficients' for the patient prior to treatment, the LASIK treatment may involve determining specific corrections to the cornea in the form of laser ablations of corneal material. The specific corrections may be represented as 'correction astigmatism coefficients' representing a targeted change in the shape of the cornea to reduce or eliminate astigmatism, for example. Accordingly, a difference of the pre-operative astigmatism coefficients and the correction astigmatism coefficients will yield 'expected astigmatism coefficients' for the LASIK treatment on the patient. In other words, the correction astigmatism coefficients, representing the LASIK correction applied during treatment, are chosen such that the expected astigmatism coefficients are as small as possible to reduce or substantially eliminate astigmatism of the patient.

However, because the cornea is a living tissue that is capable of healing, changes to the patient's cornea may be observed subsequent to LASIK treatment. The changes to the cornea after LASIK may be observed for a period of about six months, with some significant changes often being observed at one month and at three months after treatment, and lesser changes often being observed after three months after treatment. Conventional methods to determine the success, or the degree of success, of LASIK treatment for astigmatism have relied upon the patient's subjective feedback to provide a measure of the observed astigmatism. For example, standardized exams or charts are commonly used to determine a degree of astigmatism that a patient experiences, based on the patient's feedback or description of visual acuity. Because any given patient may have a widely different perception of vision than any other patient, even with similar astigmatism, it is no surprise that the targeted correction performed using LASIK may also vary widely in terms of the results achieved and the positive impact on visual acuity for any given patient. Furthermore, because perceived vision is so subjective and may also depend upon processing of visual information in the visual cortex of the brain or a lenticular ability to compensate part or totally the astigmatism of the cornea, any correlation of perceived vision to the actual corneal aberrations applied during LASIK may be tenuous at best. Furthermore, perceived astigmatism and the astigmatic axis may be subjectively influenced by other aberrations, such as vertical trefoil $Z_6$ and vertical coma $Z_7$ (see Table 1), as well as higher order astigmatism. As a result, an actual determination of the astigmatism after LASIK based on patient feedback, in order to calibrate the corrected astigmatism to actual astigmatism, may often be inaccurate and may not be statistically correlated in a given population sample.

As will be described in further detail, the inventor of the present disclosure has developed a method for calculation of actual astigmatism correction and nomographs for corneal laser treatment. The method for calculation of actual astigmatism correction and nomographs for corneal laser treatment disclosed herein may perform a subsequent corneal measurement to ascertain the actual astigmatism coefficients observed on the patient after LASIK astigmatism treatment. The method for calculation of actual astigmatism correction and nomographs for corneal laser treatment disclosed herein may use the actual astigmatism coefficients to generate nomographs that can be used to calibrate correction astigmatism coefficients that are applied during LASIK in order to result in the desired actual astigmatism coefficients for the patient.

Referring now to the drawings, FIG. 1 illustrates a depiction of an embodiment of an aberration of the cornea 100. FIG. 1 is a schematic diagram for descriptive purposes and is not drawn to scale or perspective. In aberration of the cornea 100, an optical axis 106 represents an optical axis of a human eye, while reference profile 102 may represent a spherical surface. Furthermore, anterior corneal profile 104 may represent aberrations at a surface of the cornea that are shown relative to reference profile 102. For example, when performing a corneal laser treatment, anterior corneal profile 104 may depict the resulting aberrations of the cornea. As shown, anterior corneal profile 104 is shown comprising primary spherical aberrations corresponding to Zernike coefficient $Z_{12}$ (see Table 1 below), however, it will be understood that any kind of aberrations may be applied to anterior corneal profile 104, such as for astigmatism, as described in further detail below.

Also shown in FIG. 1 are rays 108, which depict how light is expected to focus along various points falling on optical axis 106. For example, the points may be selected to correspond to a location of the retina under various optical conditions to facilitate visual acuity. In this manner, anterior corneal profile 104 may be formed to create variations in refraction of incoming rays (not shown) that will result in a desired visual acuity. Although anterior corneal profile 104 is shown as a cross-sectional profile, it will be understood that circular symmetry may be applied about optical axis 106 to represent anterior corneal surface 104 in three dimensions. It is noted that anterior corneal surface 104 may further include certain asymmetric features, such as axially dependent features, in various embodiments.

As noted previously, aberration parameters for LASIK, such as the correction astigmatism coefficients described above, may be used to calculate anterior corneal profile 104. Then, based on the aberration parameters, anterior corneal profile 104 may be created in the cornea using a laser treatment, such as LASIK. In this manner, various vision conditions may be treated and improved visual acuity may be obtained. For example, anterior corneal profile 104 may be used to treat astigmatism using LASIK.

Specifically, Zernike polynomials may be used for curve fitting of the corneal topography for calculation of actual astigmatism correction and nomographs for corneal laser treatment. Table 1 shows nomenclature for the first 15 Zernike polynomial coefficients (or simply Zernike coefficients), which may be formally designated using two indices as $Z_n^m$, where n is a radial index and m is a meridional index, and also using a single index j as $Z_j$, where $$j = \frac{n(n+2)+m}{2}.$$

TABLE 1

Nomenclature for the first 15 Zernike polynomial coefficients

| n | m | j | Z |
|---|---|---|---|
| 0 | 0 | 0 | Piston |
| 1 | −1 | 1 | Vertical Tilt |
| 1 | 1 | 2 | Horizontal Tilt |
| 2 | −2 | 3 | Oblique Primary Astigmatism |
| 2 | 0 | 4 | Defocus |
| 2 | 2 | 5 | Vertical Primary Astigmatism |
| 3 | −3 | 6 | Vertical Trefoil |
| 3 | −1 | 7 | Vertical Coma |
| 3 | 1 | 8 | Horizontal Coma |
| 3 | 3 | 9 | Oblique Trefoil |
| 4 | −4 | 10 | Oblique Tetrafoil |
| 4 | −2 | 11 | Oblique Secondary Astigmatism |
| 4 | 0 | 12 | Primary Spherical |
| 4 | 2 | 13 | Vertical Secondary Astigmatism |
| 4 | 4 | 14 | Vertical Tetrafoil |

Specifically for astigmatism, the Zernike coefficients $Z_3$, $Z_5$, $Z_{11}$, and $Z_{13}$ may be used with the corresponding Zernike aberration term that is an orthonormal polynomial function, as given below in Equations 1 to 4, in which $\rho$ is a radial point height and $\theta$ is the angular circle coordinate on a unit circle for polar coordinates (with the corresponding Cartesian coordinates (x, y) given by $x = \rho \cos\theta$ and $y = \rho \sin\theta$).

Oblique Primary Astigmatism $Z_3[\sqrt{6}\, \rho^2 \sin 2\theta]$    Equation 1

Vertical Primary Astigmatism $Z_5[\sqrt{6}\, \rho^2 \cos 2\theta]$    Equation 2

Oblique Secondary Astigmatism $Z_{11}[\sqrt{10}(4\rho^4 - 3\rho^2)\sin 2\theta]$    Equation 3

Vertical Secondary Astigmatism $Z_{13}[\sqrt{10}(4\rho^4 - 3\rho^2)\cos 2\theta]$    Equation 4

In addition to the determination of the Zernike coefficients, astigmatism is also defined by an astigmatic axis that defines an angular location of the flatter principal meridian of the cornea. The astigmatic axis may also be determined as a result of the curve fitting of the Zernike polynomials using the Zernike coefficients defined above.

Accordingly, any one or more of Zernike coefficients $Z_3$, $Z_5$, $Z_{11}$, and $Z_{13}$ may be used for calculation of actual astigmatism correction and nomographs for corneal laser treatment, as disclosed herein. Specifically, a "pre-operative astigmatism coefficient" may refer to a Zernike coefficient corresponding to the cornea prior to LASIK corneal treatment. A "correction astigmatism coefficient" may refer to a Zernike coefficient describing the changes to the cornea planned with the LASIK corneal treatment. An "expected astigmatism coefficient" may refer to an expected shape of the cornea having the pre-operative astigmatism coefficient subject to the LASIK corneal treatment using the correction astigmatism coefficient; in other words, the expected astigmatism coefficient is the difference between the pre-operative astigmatism coefficient and the correction astigmatism coefficient. An "actual astigmatism coefficient" refers to an actual post-operative astigmatism coefficient subsequent to application of the correction astigmatism coefficient using the LASIK corneal treatment. Accordingly, when the cornea is changed exactly as expected using the LASIK corneal treatment, the expected astigmatism coefficient will equal the actual astigmatism coefficient, which will be zero or nearly zero or a relatively small value. Because the cornea may not change exactly as expected, a difference between the expected astigmatism coefficient and the actual astigmatism coefficient may be used as a nomograph value to calibrate the LASIK corneal treatment.

An example nomograph calculation for Zernike coefficients $Z_3$ for an optical zone of 6.5 mm are shown for a sample population of 9 patients in Table 2. In Table 2, ACTUAL $Z_3$ values are measured 3 months after the patient has undergone LASIK corneal treatment according to CORRECTION $Z_3$. Although Table 2 shows values for oblique primary astigmatism $Z_3$, in actual practice, oblique and vertical coefficients may be used in pairs, such as $Z_3$ and $Z_5$, or $Z_{11}$ and $Z_{13}$. Because the corresponding corrections for Zernike coefficient $Z_5$, which are applied in conjunction with Zernike coefficient $Z_3$, have been omitted for descriptive clarity in Table 2, CORRECTION $Z_3$ is not always equal to PRE-OP $Z_3$.

TABLE 2

Calculation of $Z_3$ nomograph values for a sample patient population.

| PATIENT | PRE-OP $Z_3$ | CORRECTION $Z_3$ | EXPECTED $Z_3$ | ACTUAL $Z_3$ | NOMOGRAPH $Z_3$ |
|---|---|---|---|---|---|
| 1 | −0.1897 | −0.1718 | −0.0179 | −0.0863 | 0.0684 |
| 2 | 0.0192 | 0.0192 | 0 | 0.2495 | −0.2459 |
| 3 | 0 | 0 | 0 | 0.3560 | −0.3560 |
| 4 | −1.0033 | −1.0033 | 0 | 0.3901 | −0.3901 |
| 5 | 0.0780 | 0.0780 | 0 | −0.3649 | 0.3649 |
| 6 | 0.2752 | 0.2752 | 0 | 0.0171 | −0.0171 |
| 7 | −0.0422 | −0.0422 | 0 | 0.0112 | −0.0112 |
| 8 | −0.0178 | −0.0178 | 0 | 0.0382 | −0.0382 |
| 9 | 0.1072 | 0.1072 | 0 | 0.1653 | −0.1653 |

Specifically, in Table 2, a first difference is EXPECTED $Z_3$=PRE-OP $Z_3$−CORRECTION $Z_3$, and a second difference is NOMOGRAPH $Z_3$=EXPECTED $Z_3$−ACTUAL $Z_3$. Table 2 represents a small sample population that is shown for descriptive purposes. When larger populations are used, additional statistical operations may be applied to determine ACTUAL $Z_3$ versus EXPECTED $Z_3$. For example, an overall range of coefficient values may be split up into bins having a certain width, and a median value may be used as an approximation for each respective bin to generate data points. Then, a curve fitting may be applied to the data points to generate a best fit nomograph function, which may be non-linear or a higher order function (see also FIG. 2).

Although the method described above with respect to Table 2 uses Zernike polynomials for curve fitting of corneal topography, it is noted that other types of functions and corresponding coefficients may also be used, such as Fourier polynomials, or other polynomial series. Furthermore, although Table 2 is shown for $Z_3$, any one or more Zernike coefficients $Z_3$, $Z_5$, $Z_{11}$, and $Z_{13}$ may be used to generate a nomograph for astigmatism correction. While the above description has been presented for LASIK corneal correction, it will be understood that the methods described herein may be applied to various types of laser surgery on the cornea or the lens. The nomograph values described herein may accordingly be specific to a particular type or instance of a laser system used for corneal laser treatment. The nomograph values described herein may be specific to a particular surgeon, and may be used to quantify differences among individual surgeons.

Figure 2:
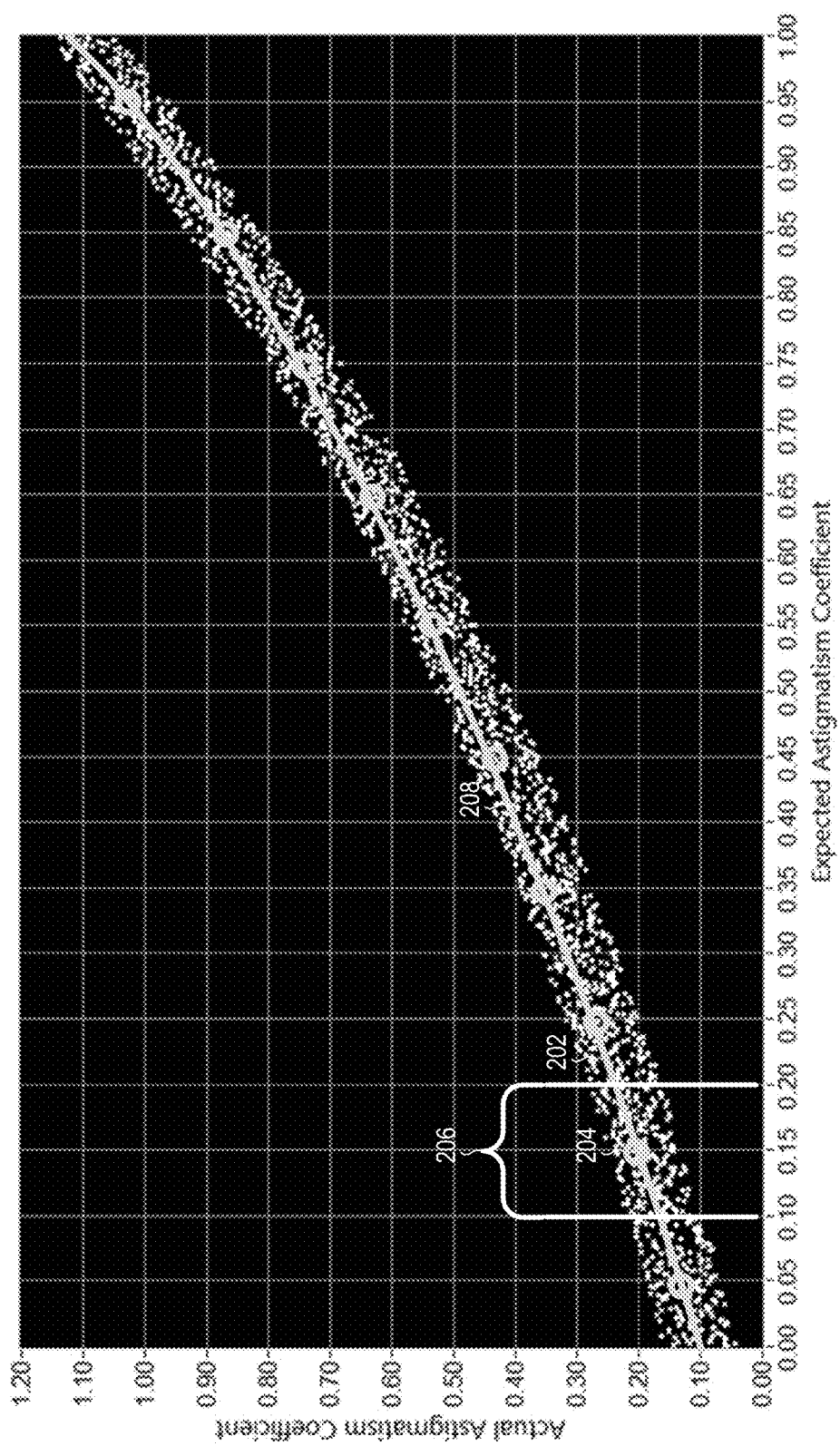
FIG. 2 is a data plot showing curve fitting for a nomograph for astigmatism coefficients.

Referring now to FIG. 2, a plot 200 showing a nomograph for astigmatism coefficients is presented. In plot 200, actual astigmatism coefficients are plotted against expected astigmatism coefficients for a sample population larger than presented above in Table 2. The values in plot 200 may be generated as described above for Table 2. It is noted that plot 200 shows simulated values for descriptive purposes, but the operations and methods described with respect to plot 200 may be equivalently used with actual clinical data from patients. Plot 200 may represent any one of Zernike coefficients $Z_3$, $Z_5$, $Z_{11}$, and $Z_{13}$, or other polynomial coefficients used to represent astigmatism.

Plot 200 is based on empirical values 202 representing actual astigmatism coefficients and corresponding expected astigmatism coefficients, such as shown above in Table 2. Empirical values 202 may be collected for a sample population of patients and plotted as in plot 200. For a given range of coefficient values, such as 0.00 to 1.00 shown in FIG. 2, the range may be subdivided into equivalent sized bins. For example, a bin 206 includes empirical values 202 between 0.10 and 0.20, having a center value at 0.15. Empirical values 202 within bin 206 may be analyzed to determine a data point 204 for the nomograph. Data point 204 may be determined by a median value of actual astigmatism coefficients within bin 206 as a Y coordinate and the center point of bin 206 (0.15) as an X coordinate. In this manner, data points 204 for each bin may be determined. Then, using data points 204, curve fitting may be applied to determine nomograph curve 208, representing an empirical function for the sample population. Then, for subsequent laser treatments, nomograph curve 208 may be used to modify the expected astigmatism coefficients to better correspond to actual astigmatism coefficients. In other words, the expected astigmatism coefficients may be scaled by a factor determined using nomograph curve 208 to yield more accurate values based on actual astigmatism coefficients.

It is noted that the generation or application of nomograph curve 208 may be integrated within a laser treatment system. For example, a processing unit (such as a controller, microprocessor, or computer system, see also FIG. 3) included within the laser treatment system may be enabled to generate nomograph curve 208, or to use nomograph curve 208 for the purposes of more exact laser treatment and to improve clinical results in reducing astigmatism.

As shown in exemplary plot 200, nomograph curve 208 is non-linear and may indicate varying levels of correction. A negative correction may occur when actual astigmatism coefficients are less than expected astigmatism coefficients, such as when the expected astigmatism coefficient is about 0.6, and the actual astigmatism coefficient is less than 0.6. A positive correction may occur when actual astigmatism coefficients are greater than expected astigmatism coefficients, such as when the expected astigmatism coefficient is about 0.9, and the actual astigmatism coefficient is greater than 0.9. Although relatively smaller percentage corrections are shown in plot 200, it will be understood that actual percentage corrections indicated by nomograph curve 208 may vary. The actual percentage corrections indicated by nomograph curve 208 may be ±5%, ±10%, ±15%, ±25%, ±30%, or ±50%, in different embodiments. In some embodiments, a positive or negative correction based on nomograph curve 208 may be greater than 50% or less than 5%.

Although not explicitly shown in FIG. 2, it will be understood that the sample population from which empirical values 202 are generated may be subdivided according to various criteria. For example, the sample population may be treated with a given instance of a particular laser treatment system. The sample population may be treated with a given type of laser treatment system, such as a particular model or laser type. The sample population may be treated by the same surgeon performing the laser treatment. The sample population may also be subdivided based on the values of the astigmatism coefficients, such as by grouping patients with similar values for the astigmatism coefficients. In this manner, nomograph curves 208 may be generated with specificity for a variety of criteria and parameters, such as in order to improve accuracy and precision.

Figure 3:
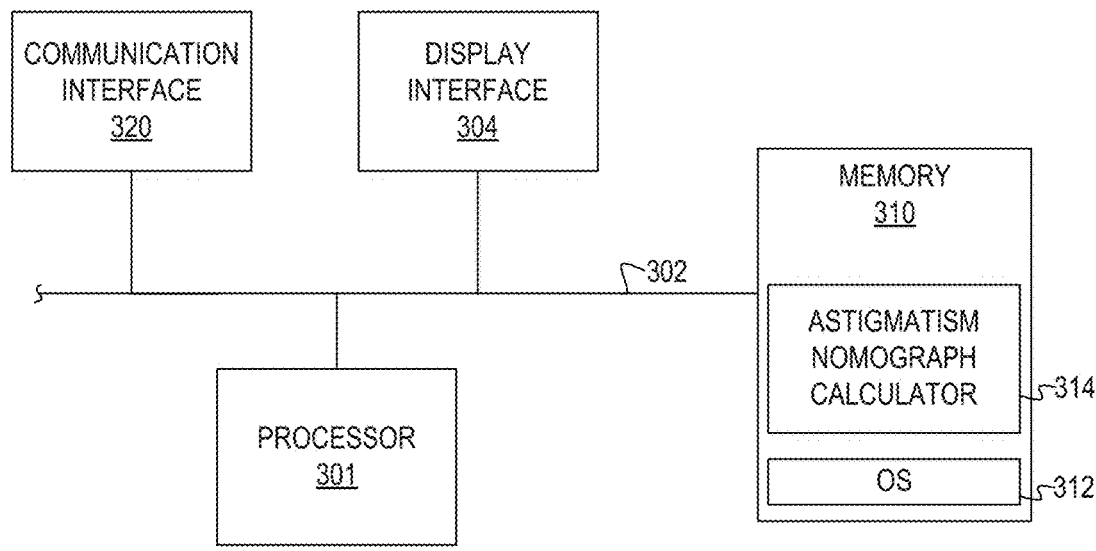
FIG. 3 is a block diagram of selected elements of an astigmatism nomograph system.

Referring now to FIG. 3, a block diagram illustrating selected elements of an embodiment of astigmatism nomograph system 300 is presented. Astigmatism nomograph system 300 may be enabled to perform calculation of actual astigmatism correction and nomograph for corneal laser treatment, as disclosed herein. In certain embodiments, astigmatism nomograph system 300 may be integrated, or coupled to, a laser treatment system, such as a LASIK system. For example, astigmatism nomograph system 300 may be used to generate or apply nomograph curve 208 for astigmatism coefficients to a planned laser treatment, as described above, by modifying expected astigmatism coefficients to result in desired actual astigmatism coefficients.

In the embodiment depicted in FIG. 3, astigmatism nomograph system 300 includes processor 301 coupled via shared bus 302 to memory media collectively identified as memory 310. Astigmatism nomograph system 300, as depicted in FIG. 3, further includes communication interface 320 that can interface to various external entities, such as laser treatment systems, among other devices. In some embodiments, communication interface 320 is operable to enable astigmatism nomograph system 300 to connect to a network (not shown in FIG. 3). In embodiments, as depicted in FIG. 3, astigmatism nomograph system 300 includes display interface 304 that connects shared bus 302, or another bus, with an output port for one or more displays.

In FIG. 3, memory 310 encompasses persistent and volatile media, fixed and removable media, and magnetic and semiconductor media. Memory 310 is operable to store instructions, data, or both. Memory 310 as shown includes sets or sequences of instructions, namely, an operating system 312, and an astigmatism nomograph calculator 314. Operating system 312 may be a UNIX or UNIX-like operating system, a Windows® family operating system, or another suitable operating system. Astigmatism nomograph calculator 314 may perform any of the various methods and calculations described herein.

Referring now to FIG. 4, a flow chart of selected elements of an embodiment of a method 400 for calculating nomographs for corneal laser treatment. It is noted that certain operations described in method 400 may be optional or may be rearranged in different embodiments. Method 400 may be performed by astigmatism nomograph system 300, for example by executing astigmatism nomograph calculator 314.

Method 400 may begin, at step 402, by calculating an expected astigmatism coefficient for a patient subject to a first corneal laser treatment as a first difference between a pre-operative astigmatism coefficient and a correction astigmatism coefficient, where the pre-operative astigmatism coefficient represents a first measurement of a cornea of the patient before the first corneal laser treatment, and the correction astigmatism coefficient represents changes to the cornea planned for the first corneal laser treatment. At step 404, an indication is received that the first corneal laser treatment on the cornea of the patient was performed according to the correction astigmatism coefficient. In some embodiments, step 402 may be omitted, while the pre-operative astigmatism coefficient and the correction astigmatism coefficient are received in step 404. At step 406, an actual astigmatism coefficient of the cornea of the patient is received, where the actual astigmatism coefficient represents a second measurement of the cornea after a time period after the first corneal laser treatment. The time period may correspond to a desired stabilization time for the cornea. The time period may be 1 month, 2 months, 3 months, 4 months, 5 months, 6 months, or greater, in various embodiments. At step 408, a nomograph value is calculated based on a second difference between the expected astigmatism coefficient and the actual astigmatism coefficient. At step 410, the nomograph value is used to calibrate the correction astigmatism coefficient for a subsequent corneal laser treatment on another patient, where the second difference for the subsequent corneal laser treatment on the other patient is smaller than the second difference for the first corneal laser treatment. The subsequent laser treatment may then be performed using the nomograph value.

As disclosed herein, a method for to calculation of actual astigmatism correction and nomographs for corneal laser treatment includes performing a post-operative measurement of the cornea of a patient to determine actual astigmatism coefficients. The actual astigmatism coefficients are compared against the expected astigmatism coefficients to generate a nomograph value or a nomograph curve over a sample population. The nomograph is used to calibrate subsequent laser treatments for improved accuracy of clinical results.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method for calculating nomographs for corneal laser treatments, the method comprising:
   calculating an expected astigmatism coefficient for a patient subject to a first corneal laser treatment as a first difference between a pre-operative astigmatism coefficient and a correction astigmatism coefficient, wherein the pre-operative astigmatism coefficient represents a first measurement of a cornea of the patient before the first corneal laser treatment, and the correction astigmatism coefficient represents changes to the cornea planned for the first corneal laser treatment;
   receiving an indication that the first corneal laser treatment on the cornea of the patient was performed according to the correction astigmatism coefficient;
   receiving an actual astigmatism coefficient of the cornea of the patient, wherein the actual astigmatism coefficient represents a second measurement of the cornea after a time period after the first corneal laser treatment; and
   calculating a nomograph value based on a second difference between the expected astigmatism coefficient and the actual astigmatism coefficient; and
   using the nomograph value to calibrate the correction astigmatism coefficient for a subsequent corneal laser treatment on another patient, wherein the second difference for the subsequent corneal laser treatment on the other patient is smaller than the second difference for the first corneal laser treatment;
   wherein the nomograph value is calculated based on a sample population of patients, wherein the pre-operative astigmatism coefficient, the correction astigmatism coefficient, the expected astigmatism coefficient, the actual astigmatism coefficient, and the second difference are determined for each patient in the sample population, and wherein the sample population is divided into bins based on the actual astigmatism coefficients and the expected astigmatism coefficients.

2. The method of claim 1, wherein the nomograph value is specific to a laser system for performing the corneal laser treatment and the subsequent corneal laser treatment.

3. The method of claim 1, wherein the nomograph value is specific to a surgeon performing the corneal laser treatment and the subsequent corneal laser treatment.

4. The method of claim 1, wherein the nomograph value is specific to a type of the corneal laser treatment and the subsequent corneal laser treatment.

5. The method of claim 1, wherein the nomograph value is calculated as an empirical function of the actual astigmatism coefficient versus the expected astigmatism coefficient for the sample population.

6. The method of claim 5, wherein a data point of the empirical function is determined using a median value of the actual astigmatism coefficient for each bin.

7. The method of claim 6, wherein the empirical function is calculated using curve fitting of a plurality of the data points.

8. The method of claim 1, wherein the pre-operative astigmatism coefficient, the correction astigmatism coefficient, the expected astigmatism coefficient, the actual astigmatism coefficient are a Zernike coefficient selected from one of: $Z_3$, $Z_5$, $Z_{11}$, and $Z_{13}$.

9. The method of claim 1, wherein the time period is three months.

10. An astigmatism nomograph system, the system comprising:
a processor having access to memory media storing instructions executable by the processor to:
calculate an expected astigmatism coefficient for a patient subject to a first corneal laser treatment as a first difference between a pre-operative astigmatism coefficient and a correction astigmatism coefficient, wherein the pre-operative astigmatism coefficient represents a first measurement of a cornea of the patient before the first corneal laser treatment, and the correction astigmatism coefficient represents changes to the cornea planned for the first corneal laser treatment;
receive an indication that the first corneal laser treatment on the cornea of the patient was performed according to the correction astigmatism coefficient;
receive an actual astigmatism coefficient of the cornea of the patient, wherein the actual astigmatism coefficient represents a second measurement of the cornea after a time period after the first corneal laser treatment; and
calculate a nomograph value based on a second difference between the expected corneal astigmatism coefficient and the actual astigmatism coefficient; and
use the nomograph value to calibrate the correction astigmatism coefficient for a subsequent corneal laser treatment on another patient, wherein the second difference for the subsequent corneal laser treatment on the other patient is smaller than the second difference for the first corneal laser treatment;
wherein the nomograph value is calculated based on a sample population of patients, wherein the pre-operative astigmatism coefficient, the correction astigmatism coefficient, the expected astigmatism coefficient, the actual astigmatism coefficient, and the second difference are determined for each patient in the sample population, and wherein the sample population is divided into bins based on the actual astigmatism coefficients and the expected astigmatism coefficients.

11. The astigmatism nomograph system of claim 10, wherein the nomograph value is specific to a laser system for performing the corneal laser treatment and the subsequent corneal laser treatment.

12. The astigmatism nomograph system of claim 10, wherein the nomograph value is specific to a surgeon performing the corneal laser treatment and the subsequent corneal laser treatment.

13. The astigmatism nomograph system of claim 10, wherein the nomograph value is specific to a type of the corneal laser treatment and the subsequent corneal laser treatment.

14. The astigmatism nomograph system of claim 10, wherein the nomograph value is calculated as an empirical function of the actual astigmatism coefficient versus the expected astigmatism coefficient for the sample population.

15. The astigmatism nomograph system of claim 14, wherein a data point of the empirical function is determined using a median value of the actual astigmatism coefficient for each bin.

16. The astigmatism nomograph system of claim 15, wherein the empirical function is calculated using curve fitting of a plurality of the data points.

17. The astigmatism nomograph system of claim 10, wherein the pre-operative astigmatism coefficient, the correction astigmatism coefficient, the expected astigmatism coefficient, the actual astigmatism coefficient are a Zernike coefficient selected from one of: $Z_3$, $Z_5$, $Z_{11}$, and $Z_{13}$.

18. The astigmatism nomograph system of claim 10, wherein the time period is three months.

* * * * *